(12) United States Patent
Mulshine et al.

(10) Patent No.: US 6,756,399 B2
(45) Date of Patent: Jun. 29, 2004

(54) USE OF LIPOXYGENASE INHIBITORS AND PPAR LIGANDS AS ANTI-CANCER THERAPEUTIC AND INTERVENTION AGENTS

(75) Inventors: James L. Mulshine, Bethesda, MD (US); Marti Jett, Washington, DC (US)

(73) Assignees: The United States of America as represented by the Department of Health and Human Services, Washington, DC (US); The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 10/186,070

(22) Filed: Jun. 28, 2002

(65) Prior Publication Data

US 2003/0082108 A1 May 1, 2003

Related U.S. Application Data

(60) Provisional application No. 60/302,155, filed on Jun. 29, 2001.

(51) Int. Cl.[7] .............................................. A61K 31/40
(52) U.S. Cl. ....................... 514/418; 514/369; 514/381; 514/419
(58) Field of Search ................................ 514/418, 381, 514/369, 419

(56) References Cited

U.S. PATENT DOCUMENTS

| | | | |
|---|---|---|---|
| 4,661,505 A | * | 4/1987 | Marshall et al. ............ 514/381 |
| 6,071,949 A | * | 6/2000 | Mulshine et al. ........... 514/418 |
| 6,187,814 B1 | | 2/2001 | Elias et al. |
| 6,242,196 B1 | * | 6/2001 | Spiegelman et al. ......... 435/7.1 |
| 6,294,559 B1 | * | 9/2001 | Smith ......................... 514/369 |
| 6,316,465 B1 | * | 11/2001 | Pershadsingh et al. ...... 514/310 |
| 2001/0036955 A1 | * | 11/2001 | Gerritsen et al. ........... 514/369 |
| 2002/0006950 A1 | * | 1/2002 | Spiegelman et al. ........ 514/401 |
| 2002/0013368 A1 | * | 1/2002 | Collin et al ................. 514/558 |
| 2002/0111373 A1 | * | 8/2002 | Fujita et al. ................. 514/369 |

FOREIGN PATENT DOCUMENTS

| | | |
|---|---|---|
| WO | WO 95/24894 | 3/1995 |
| WO | WO 98/25598 | 12/1997 |
| WO | WO 98/29113 | 12/1997 |

OTHER PUBLICATIONS

Tsubouchi et al., "Inhibition of Human Lung Cancer Cell Growth by the Peroxisome Proliferator–Activated Receptor–γ Agonists Through Induction of Apoptosis," *Biochemical and Biophysical Research Communications*, vol. 270, No. 2, pp. 400–405 (2000).

* cited by examiner

*Primary Examiner*—James H Reamer
(74) *Attorney, Agent, or Firm*—Klarquist Sparkman, LLP

(57) ABSTRACT

The present invention provides a method for treating and preventing an epithelial cell-derived cancer in a subject in need thereof, comprising administering to the subject an amount of a 5-lipoxygenase inhibitor and PPAR ligand or derivatives thereof, effective to treat or prevent the epithelial cell-derived cancer. Also encompassed by the invention are inhibitors of enzymes that metabolize arachidonic acid.

55 Claims, 2 Drawing Sheets

USE OF LIPOXYGENASE INHIBITORS AND PPAR LIGANDS AS ANTI-CANCER THERAPEUTIC AND INTERVENTION AGENTS

This application claims priority under 35 U.S.C. §119(e) for Provisional Application No. 60/302,155, filed on Jun. 29, 2001 by Mulshine, J. et al., entitled "Use Of Lipoxygenase Inhibitors And PPAR Ligands As Anti-Cancer Therapeutic And Intervention Agents."

FIELD OF THE INVENTION

The present invention is in the field of the prevention and treatment of cancer. More specifically, this invention relates to the use of 5-lipoxygenase inhibitors and PPAR ligands or derivatives thereof in preventing and treating cancer.

BACKGROUND OF THE INVENTION

The lifetime risk of breast cancer in American women is higher than for any other malignancy (1). A variety of metabolic and hormonal factors, including dietary fat, are postulated to have a promotional effect on the progression of breast cancer, but how these factors contribute to the pathogenesis of the disease process is not understood (2–4). Growth factors can function as survival factors and have been reported to inhibit apoptosis (5–7). Insulin-like growth factor-1(IGF-1) is an important growth factor for breast cancer. Activation of the IGF-type 1 receptor (IGF-R), possibly through the action of phosphatidylinositol 3-kinase has been suggested to be a critical tumor promotion and survival factor (8–13). Previously, the over-expression of IGF-R and its ligand were reported as conserved features of both breast and lung cancer (14). Blocking the 5-LO pathway of arachidonic acid (AA) metabolism in lung cancer (15) was reported to neutralize IGF-1-dependent growth stimulation and survival effects.

The AA metabolizing enzymes are emerging as significant mediators of growth stimulation for epithelial cells. Earashi and Noguchi suggested that AA metabolism may play a significant role in mammary carcinogenesis through oxidative processes (16, 17), and Przyipiak and co-workers evaluated the effects of 5-LO on the proliferation of MCF-7 cells (18). AA can be metabolized either by the COX or the LO pathways and knowledge about the enzymes responsible for both metabolic routes is rapidly increasing (19–21). As part of a general epithelial survey, the relative frequency of expression of five AA metabolizing enzymes and FLAP in breast cancer cells was established (22). Biologically active products of the 5-LO pathway include 5-HETE and leukotrienes, which contribute to the inflammatory process in a variety of diseases. A number of pharmacological antagonists for the AA pathways are available which act by different mechanisms. The regulation of 5-LO products can be achieved either by direct inhibition of the enzyme such as with the competitive inhibitor AA 861, Zileuton or by the phenol redox inhibitor, NDGA. In addition there exists another class of selective 5-LO inhibitors, MK 886 and MK 591, which are thought to inhibit indirectly by interacting with FLAP and interfering with the presentation of AA to the 5-LO enzyme at the nuclear envelope membrane (20, 23).

There have been reports regarding the mechanistic basis of the anti-proliferative effect of the FLAP inhibitor (26). Induction of differentiation and apoptosis in cancer cells can also occur through the action of other oxidation products of AA. The peroxisome proliferator-activated receptors (PPARs) are members of the nuclear hormone receptor subfamily of transcription factors. The PPARs were originally identified as orphan receptors, without known ligands, but were named for their ability to mediate the pleiotropic effects of fatty acid peroxisome proliferators. PPARs form heterodimers with other members of the nuclear hormone receptor superfamily and these heterodimers regulate the transcription of various genes. There are 3 related types of PPARs, PPARα, PPARδ, and two isoforms of PPARγ.

Further, PPARs are activated by long chain fatty acids and synthetic ligands, which regulate lipid metabolism and have been further shown to be expressed in breast cancer cells (27). More specifically, elevated expression of PPARγ has been demonstrated in human primary and metastatic breast adenocarcinomas (27) and in Alzheimer's disease brains (28) while allelic variants have been reported in sporadic colon cancers (29). The pharmacological modulation of PPARγ expression and/or function may therefore be an appropriate point of therapeutic intervention in pathological conditions.

SUMMARY OF THE INVENTION

The present invention generally relates to the use of lipoxygenase inhibitors and PPAR ligands in therapeutic applications, in particular to the prevention and treatment of epithelial cell-derived cancers.

The present invention also provides a method for treating an epithelial cell-derived cancer in a subject in need of such treatment which comprises administering to the subject an amount of an inhibitor of a 5-lipoxygenase enzymatic function and a PPAR ligand effective to treat the epithelial cell-derived cancer.

It is also an object of the present invention to provide a method for preventing an epithelial cell-derived cancer in a subject in need of such prevention which comprises administering to the subject an inhibitor of a 5- lipoxygenase enzymatic function and a PPAR ligand effective to prevent the epithelial cell-derived cancer.

It is yet another object of the invention to provide a method for preventing an epithelial cell-derived cancer in a subject in need of such prevention which comprises administering to the subject in need thereof, an amount of an inhibitor of an enzyme that metabolizes arachidonic acid and a molecule subject to transcriptional regulation by binding of RXR heterodimers or variants thereof effective to prevent an epithelial cell-derived cancer.

It is yet another object of the invention to provide a method for treating an epithelial cell-derived cancer in a subject in need of such prevention which comprises administering to the subject in need thereof, an amount of an inhibitor of an enzyme that metabolizes arachidonic acid and a molecule subject to transcriptional regulation by binding of RXR heterodimers or variants thereof effective to treat an epithelial cell-derived cancer.

It is yet another object of this invention to provide pharmaceutical compositions comprising a 5-lipoxygenase inhibitor, PPAR ligand, or derivatives thereof, for the methods described herein.

DESCRIPTION OF THE INVENTION

Figure 1:
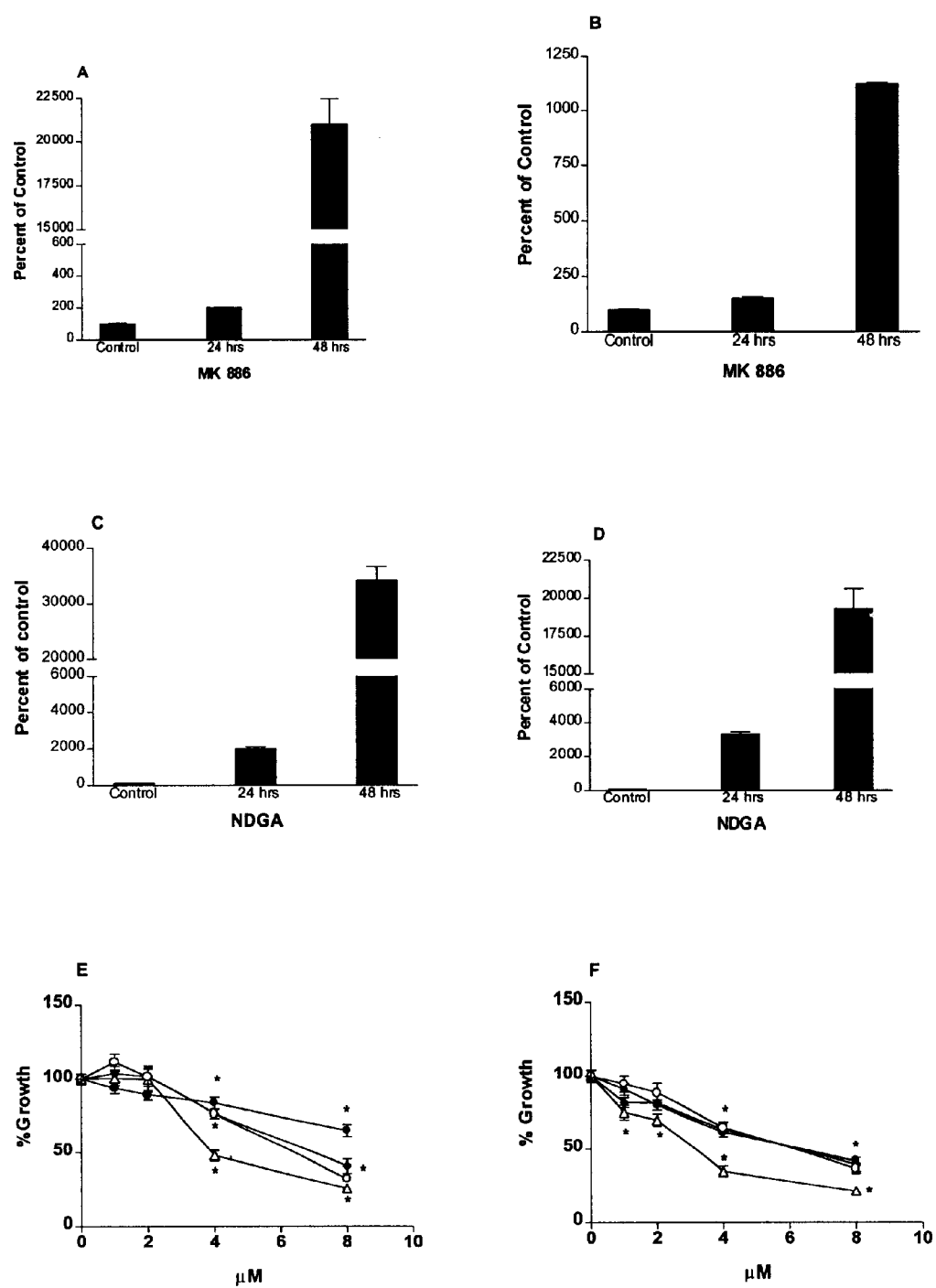
FIG. 1 shows the effect of 5-LO inhibitors on PPAR expression status (A–D), and effect of increased PPAR activation on in vitro breast cancer cell line growth (E, F). Breast cancer cell line ZR-75 was grown in the presence of 5 μM inhibitors for 24 and 48 hrs, total RNA was isolated and RT-PCR performed for PPARα and PPARγ using specific primers. Results are presented as percent of control after normalizing with the actin values. The experiment was repeated three times. The error bars indicate standard deviation. The first row (A, B) shows the effect of MK 886 on PPARα and PPARγ at baseline, 24 and 48 hours. The second row shows the effect of NDGA on PPARα (C) and PPARγ (D) under the same conditions as above. The third row (E, F) shows the growth inhibitory effect of PPAR ligands on breast cancer cell line ZR-75 (E) and T47D (F), as evaluated using a proliferation assay. All values were determined by assessment of % growth inhibition calculated from the optical density value, with a minimum of 6 replicates from at least three different experiments per cell line. The ligands included WY-14643 (open circles); LY 171883 (closed circles); fenofibrate (triangles); clofibrate (diamonds). The error bars indicate standard deviation. *The values were significantly different from control (P<0.05).

The present invention provides a method for treating or preventing an epithelial cell-derived cancer in a subject in need thereof which comprises administering to the subject an amount of a 5-lipoxygenase inhibitor and peroxisome proliferator-activated receptor (PPAR) ligand, or derivative thereof, effective to treat or prevent the epithelial cell-derived cancer. The invention further provides a method for treating or preventing an epithelial cell-derived cancer in a subject in need thereof by administering an effective amount of an inhibitor of other enzymes involved in the metabolism of arachidonic acid in the 5-lipoxygenase signaling pathway and a PPAR ligand which comprises administering to the subject an amount of the inhibitor and ligand effective to treat or prevent an epithelial cell-derived cancer.

The term "treatment" includes partial or total inhibition of the cancer growth, as well as partial or total destruction of the cancer cells.

The term "prevention" includes either preventing the onset of clinically evident cancer altogether, or delaying its onset.

In the methods of the invention, epithelial cell-derived cancer (epithelial carcinoma) includes basal cell carcinoma, adenocarcinoma, renal cell carcinoma, and other known cancers that effect epithelial cells throughout the body. In one preferred embodiment of the invention, epithelial cell-derived cancers comprise breast and lung cancers. Other tissue types that are contemplated for the treatment and prevention of epithelial cell-based cancers include colon, prostate, uterine, and cervical cancers.

The term "subject" for purposes of treatment includes any mammal, human or animal subject, who has any one of the known epithelial cell-derived cancers, and preferably is a human. For methods of prevention, the subject is preferably any human or animal subject, and preferably is a human subject who is at risk for developing an epithelium cell-derived cancer. The subject may be at risk due to exposure to carcinogenic agents, being genetically predisposed to have the cancer, and the like.

Inhibitors of the 5-lipoxygenase (5-LO) pathway in the metabolism of arachidonic acid and PPAR ligands used in the prevention and treatment of epithelial cell-derived cancers may inhibit enzyme activity through a variety of mechanisms. By way of example, the inhibitor may block or reverse the association of the enzyme with the membrane or inhibit the translocation of specific enzymes such as 5-LO via a protein such as 5-LO activating protein (FLAP) and concurrently stimulate, activate, or produce PPAR ligands. Alternatively, the inhibitors used in the methods described herein may block the enzyme activity directly by acting as a substrate for the enzyme or by depriving the enzyme of necessary cofactors.

In preferred embodiments, the 5-lipoxygenase inhibitor is 3-[1-(4-chlorobenzyl)-3-t-butyl-thio-5-isopropylindol-2-yl]-2,2-dimethylpropanoic acid (MK886) (30–31) or derivatives thereof; 3-(1-(4-chlorobenzyl)-3-(1-butyl-thio)-5-(quinolin-2-yl-methoxy)-indol-2-yl)-2,2-dimethyl propanoic acid) (MK-591) (32) or derivatives thereof; Nor-dihydroguaiaretic acid (NDGA) (33–34) or derivatives thereof; or 2-(12-Hydroxydodeca-5,10-diynyl)-3,5,6-trimethyl-1,4-benzoquinone (AA861) (35–36) or derivatives thereof.

In one embodiment, derivatives of 5-LO inhibitors are intended to encompass any compounds which are structurally related to 5-LO inhibitors, including MK886, MK591, NDGA or AA861 which possess the substantially equivalent biologic activity of MK886, MK591, NDGA, or AA861. By way of example, such inhibitors may include, but are not limited to, derivatives that act as co-factor antagonist, better enzymatic substrates or inhibitors of activating peptide function.

In yet another embodiment, derivatives of MK886 intended to be encompassed by this invention include, but are not limited to, L-669,572 3-[1-(p-cholorobenzyl)-5-isopropyl-3-cyclo-propylmethylthioindole-2-yl]-2,2-dimethylpropanoic acid; L-663,511 3-[1-(p-cholorobenzyl)-5-isopropyl-3-phenysulfonylindol-2-yl)-2,2-dimethyl propanoic acid, L-665,210, 3-[1-(p-chlorobenzyl)-5-isopropyl-3-phenysulfonylindol-2-yl)-2,2-dimethyl pro-panoic aid; L-654-639, 3[1-(p-chlorobenzyl)-5-methoxy-3-methylindol-2-yl]-2,2-dimethylpropanoic acid; and L-668, 017 described in Rouzer et al. (31) which is herein incorporated by reference. In a preferred embodiment, the MK886 derivative is 3-1-(4-chlorobenzyl)-3-(1-butyl-thio)-5-(quinolin-2-yl-methoxy)-indol-2-y l)-2,2-dimethyl propanoic acid) (MK-591) (32).

In yet another embodiment of this invention, hydroxyurea derivatives are contemplated as inhibitors of 5-lipoxygenase in the prevention and treatment of epithelial cell-derived cancers. Examples of hydroxyurea derivatives include, but are not limited to, (N-(1-benzo(b)thien-2-ylethyl)-N-hydroxyurea) (Zieuton) (32) herein incorporated by reference.

Another embodiment of this invention relates to inhibitors of other enzymes that metabolize arachidonic acid downstream of 5-lipoxygenase in combination with PPAR ligands. Such inhibitors may affect the activity of the enzyme either directly by acting as a substrate inhibitor or by depriving the enzyme of a cofactor. The inhibitor may also act by targeting proteins such as FLAP which are responsible for the translocation of the enzymes to the membrane where the enzymes are activated. Inhibitors of 5-LO are used with PPAR ligands for the inhibition and prevention of epithelial cell-derived cancers.

Any of the known PPAR ligands can be used in the present invention. In preferred embodiments, the PPAR ligands are PPARα or PPARγ. More specifically, PPAR ligands or derivatives thereof are WY-14643 (4-chloro-6-(2,3-xylidino)-2-pyrimidinylthio acetic acid), clofibrate (2-(4-chlorophenoxy)-2-methylpropanoic acid ethyl ester), fenofibrate (2-(4-[4-Chlorobenzoyl]phenoxy)-2-methylpropanoic acid), and LY171883 ($C_{16}H_{22}N_4O_3$). Other PPAR ligands further include 15d-PGJ$_2$ (15-Deoxy-$\Delta^{12,14}$-Prostaglandin J$_2$), ciglitazone ((±)-5-[4-(1-Methylcyclohexylmethoxy)-benzyl] thiazolidine-2,4-dione), and troglitazone ((±)-5-[4-[(6-hydroxy-2,5,7,8-tetramethylchroman-2-yl) methoxy]-benxyl]-2,4-thiazolidinedione).

Derivatives of PPAR ligands are preferably intended to encompass any compounds which are structurally related to WY-14643 (4-chloro-6-(2,3-xylidino)-2-pyrimidinylthio acetic acid), clofibrate (2-(4-chlorophenoxy)-2-methylpropanoic acid ethyl ester), fenofibrate (2-(4-[4-Chlorobenzoyl]phenoxy)-2-methylpropanoic acid), LY171883 ($C_{16}H_{22}N_4O_3$), 15d-PGJ$_2$ (15-Deoxy-$\Delta^{12,14}$-Prostaglandin J$_2$), ciglitazone ((±)-5-[4-(1-Methylcyclohexylmethoxy)-benzyl] thiazolidine-2,4-dione), or troglitazone ((±)-5-[4-[(6-hydroxy-2,5,7,8-tetramethylchroman-2-yl) methoxy]-benxyl]-2,4-thiazolidinedione), or which possess the substantially equivalent biologic activity of WY-14643 (4-chloro-6-(2,3-xylidino)-2-pyrimidinylthio acetic acid), clofibrate (2-(4-chlorophenoxy)-2-methylpropanoic acid ethyl ester), fenofibrate (2-(4-[4-Chlorobenzoyl]phenoxy)-2-methylpropanoic acid), LY171883 ($C_{16}H_{22}N_4O_3$), 15d-PGJ$_2$ (15-Deoxy-$\Delta^{12,14}$-Prostaglandin J$_2$), ciglitazone ((±)-5-[4-(1-Methylcyclohexylmethoxy)-benzyl] thiazolidine-2,4-dione), or troglitazone ((±)-5-[4-[(6-hydroxy-2,5,7,8-tetramethylchroman-2-yl) methoxy]-benxyl]-2,4-thiazolidinedione).

In a further embodiment of the invention, other modulators of PPAR-γ function are contemplated and include, for example, the use of antibodies and the administration of synthetic and naturally occurring ligands that act as agonists. PPAR-γ is activated by a range of synthetic and naturally occurring substances including thiazolidinediones (TZDs) (37–42), phenylacetic acid derivatives (43–44), fatty acids (45), prostaglandins (46–47) and components of oxidized low-density lipoproteins (48).

The present invention provides a method of inhibiting and/or preventing the growth of epithelial cell-derived cancer cells by administering an inhibitor to an enzyme that metabolizes arachidonic acid and PPAR ligand, either sequentially or simultaneously. Preferably the inhibitor and ligand are administered sequentially and more preferably, the 5-LO inhibitor is administered first. The combination of 5-LO inhibitor and PPAR ligand may be used for preventative and/ or therapeutic purposes. When provided preventatively, or prophylactically, the 5-LO inhibitor and PPAR ligand are provided in advance of any evidence or symptom in the mammal due to cancer, in particular, epithelial cell-derived cancers. The prophylactic use of the 5-LO inhibitor and PPAR ligand serves to prevent or attenuate the cancer in a mammal, preferably human. Also, the present invention comprises a method of preventing the growth of epithelial cell-derived cancer cells in a subject in need thereof by administering a 5-LO inhibitor and a PPAR ligand, either sequentially or simultaneously, in an amount effective to induce apoptosis.

Further, the 5-LO inhibitor and PPAR ligand may be therapeutically provided after the onset of a disease, preferably an epithelial cell-derived cancer, in a mammal. The therapeutic administration of the 5-LO inhibitor and PPAR ligand serves to attenuate the disease. A method of treating a subject, preferably human, having an epithelial cell-derived cancer, with a 5-LO inhibitor and PPAR ligand comprises administering to the subject in need thereof, an effective amount of 5-LO inhibitor and PPAR ligand to attenuate the disease. Also, a method of treating an epithelial cell-derived cancer in a subject in need thereof, comprising administering a 5-LO inhibitor and PPAR ligand, either sequentially or simultaneously, in an amount effective to induce apoptosis. Sequential drug exposure is preferred and was found to be more potent than either single drug exposure alone. This finding was observed in breast cancer studies, and to a lesser extent in lung cancer experiments. See e.g. Examples 2 and 4. For breast cancer, the enhanced inhibition with the combined drug administration may be at least partially due to the PPAR γ induction observed after exposure of the breast cancer cells to the 5-LO inhibitor.

In a more preferred embodiment of the invention, methods for preventing or treating the growth of epithelial cell-derived cancers in a subject in need thereof, comprise sequentially administering a 5-LO inhibitor of the formula, 3-[1-(4-chlorobenzyl)-3-t-butyl-thio-5-isopropylindol-2-yl]-2,2-dimethylpropanoic acid, or a derivative thereof and administering a PPARγ ligand, preferably LY171883.

The administration for the above methods may be affected by means known to those skilled in the art such as oral, rectal, topical, intranasal, intravenous, subcutaneous, intramuscular, intrabronchial, intracavitary, or intraperitoneal routes of administration. If the cancer is localized, local administration rather than systemic administration is preferred. Formulation in a lipid vehicle may be used to enhance bioavailability. The most preferred method of administration is by aerosal spray.

For aerosol delivery, the compounds may be formulated with known aerosol excipients, such as saline, alcohol, or other gras (generally recognized as safe) agents, and administered using commercially available nebulizers or hand-held devices. Formulation in a fatty acid source may be used to enhance biocompatibility. Aerosol delivery is a preferred method of delivery for epithelial cancers of the breast and lung for preventative applications. Since the compound of interest can be localized directly to these epithelial cells, and bypasses the digestive/ circulatory systems, aerosol delivery is a preferred administration method. Further, a greater fraction of the administered dose may reach the target tissue, thereby lowering the preventative and/or therapeutic dosage while reducing the potential for side effects.

For oral administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

The compounds utilized in the methods of the present invention may be present in the form of free bases or pharmaceutically acceptable acid addition salts thereof. Examples of suitable acids for salt formation are: methanesulfonic, sulfuric, hydrochloric, phosphoric, acetic, citric, lactic, ascorbic, maleic, and the like.

If the cancer is localized in the gastric intestinal tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like.

For rectal, uterine, cervical administration, the active ingredient may be formulated into suppositories using bases which are solid at room temperature and melt or dissolve at body temperature. Commonly used bases include coca butter, glycerinated gelatin, hydrogenated vegetable oil, polyethylene glycols of various molecular weights, and fatty esters of polyethylene stearate.

The dosage form and amount can be readily established by reference to known cancer prevention and treatment. The dosage for the inhibitors or derivatives thereof may be from about 0.1 ng/kg to about 450 mg/kg, more preferred is about 0.5 ng/kg to about 100 mg/kg, and most preferably is about 1 ng/kg to about 25 mg/kg. Dosage is preferably such that 1–5 µM of the preferred drug is in interstitial fluid of the bronchial epithelium, where one skilled in the art can readily calculate the appropriate amount of drug to achieve such levels. The actual dose will depend upon the administration for prevention and treatment, the route of administration, the location of the cancer, as well as the pharmacokinetic properties of the individual treated. The dosage will generally be lower if the compounds are administered locally rather than systemically. Such treatments may be administered as often as necessary and for the period of time judged necessary by the treating physician. One of skill in the art will appreciate that the dosage regime or therapeutically effective amount of the inhibitor to be administrated may need to be optimized for each individual.

The administration of the present invention may be for prevention and treatment purposes. The methods and compositions used herein may be used alone or in conjunction with additional therapies known to those skilled in the art in the prevention and treatment of cancer. Alternatively, the methods and compositions described herein may be used as adjunct therapy. By way of example, the 5-lipoxygenase inhibitor and PPAR ligand may be administered in conjunction with other agents or other growth inhibiting agents or other drugs or nutrients. Alternatively, the PPAR ligand and the 5-lipoxygenase inhibitor or derivatives thereof and the inhibitor of other downstream enzymes involved in the metabolism of arachidonic acid, also known as arachidonate, may be administered in combination with each other, either sequentially or simultaneously, preferably simultaneously.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The invention will now be illustrated by the following non-limiting examples.

EXAMPLE 1

Reagents

Synthetic 5-HETE, 5-LO inhibitors NDGA and AA861, and the FLAP inhibitor MK 886 were obtained from BIO-MOL Research Laboratories (Plymouth Meeting, Pa.). The novel FLAP antagonist MK 591 was a kind gift from Merck Frosst Centre for Therapeutic Research (Pointe Claire-Dorval, Quebec, Canada) and Zileuton was kindly provided by the NCI Chemoprevention Drug Repository, Rockville, Md. The COX inhibitor, ASA, as well as, PPAR ligands, clofibrate and fenofibrate, were purchased from Sigma Chemicals (St. Louis, Mo.). PPAR ligands LY 171883, and WY-14643 were purchased from BIOMOL Research Laboratories, Inc. (Plymouth Meeting, Pa.).

Cell Lines

Cell lines used in the study were obtained from the American Type Culture Collection (Rockville, Md.). They included MCF-7, ZR-75, T47 D; SKBR-3, and MB-231. The cells were maintained in RPMI-1640, or MEM Zinc option medium, supplemented with 5% fetal bovine serum (FBS), penicillin (50 units/ml) and streptomycin (50 µg/ml) (Life Technologies, Gaithersburg, Md.), in a humidified atmosphere of 95% air and 5% $CO_2$ at 37° C.

Statistical Evaluation

Significance of difference between samples was determined using Student's t test. $P<0.05$ was regarded as significant.

EXAMPLE 2

PCR-Based RNA Analyses for PPAR

Cells were grown for 24 hrs or 48 hrs in the presence or absence of inhibitors at 5 µM concentration. RNA was isolated using the Trizol method (Life Technologies, Gaithersburg, Md.), and RT-PCR was performed using specific primers for PPAR and actin control genes.

Forward (F) and reverse (R) primers used to detect PPAR cDNAs were:

| | |
|---|---|
| PPAR α-F (5'-GGCCTCAGGCTATCATTAC-3') | (SEQ ID NO:1) |
| PPAR α-R (5'-CCATTTCCATACGCTACC-3') | (SEQ ID NO:2) |
| PPAR γ-F (5'-TTCAAACACATCACCCCCC-3') | (SEQ ID NO:3) |
| PPAR γ-R (5'-TTGCCAAGTCGCTGTCATC-3') | (SEQ ID NO:4) |

The ethidium bromide stained image was digitized and the optical density calculated using the NIH Image program. Values were normalized with the actin value obtained with commercially available primers (Clontech Inc., Palo Alto, Calif. ). These experiments were repeated three times.

PPAR induction

Figure 2:
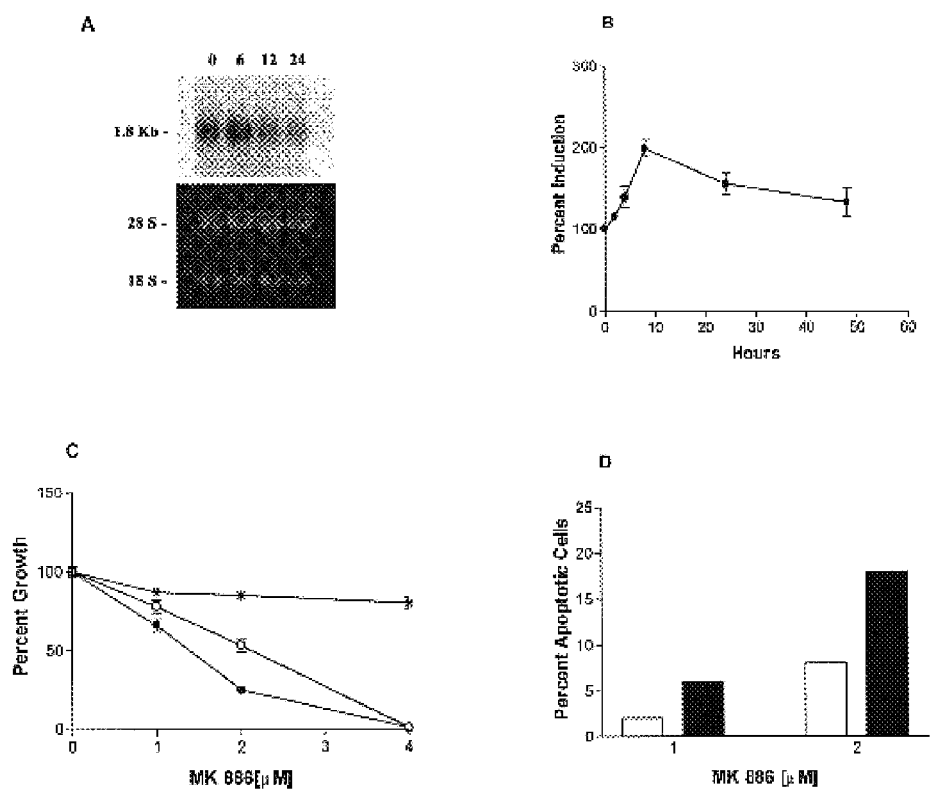
FIG. 2 shows the factors contributing to breast cancer growth inhibition or apoptosis after exposure to 5-LO inhibitors. (A) Northern blot analysis for PPARγ (1.8 Kb), of breast cancer cell line T47D treated with 5 μM MK 886 for 6, 12, 24 hrs and untreated control. RNA was isolated as described in Methods, and 10 μM of total RNA was loaded per lane. Ethidium bromide staining of 28S rRNA was used to check for equal loading and RNA integrity (lower panel). (B) RNA isolated from T47D cells treated with 5 μM MK 886 for different time periods were subjected to RT-PCR using specific primers for PPARγ. The PCR products were normalized to actin gene and 18S. PCR products were quantified by densitometry and the data points presented are expressed as percent of control, and represent mean and SEM of three experiments. (C) Breast cancer cell line T47D, was incubated with various concentrations of MK886 (circles) and then analyzed using a proliferation assay. After 12 hr incubation, the inhibitors were removed and replaced by media alone (open circles), or media with 4 μM LY 171883 (closed circles). LY 171883 in the presence of media without the FLAP inhibitor is shown (stars). After an additional 24 hr incubation time, the experiments were terminated. All values were determined by assessment of % growth inhibition calculated from the optical density value, with a minimum of 6 replicates from at least three different experiments. The error bars indicate standard deviation. (D) Parallel experiments were performed as described for (C) to evaluate the effects on apoptosis as reflected by the early apoptosis marker M30, (Roche Molecular Biochemicals, Indianapolis, Ind.). Open bars represent apoptosis with treatment of MK 886 alone; filled bars represent sequential treatment with MK 886 and 4 μM LY 171883. Results are presented as percent apoptotic cells for two concentrations of MK 886.

In light of recent reports regarding the mechanistic basis of the anti-proliferative effect of the FLAP inhibitor (26), alternative mechanisms for the growth effects on 5-LO inhibition was explored. A large increase in 15-HETE production in response to the exposure to MK 886 (FIG. 2) was observed, and 15-HETE has been proposed to be a ligand for PPARγ (48). When the breast tumor cell line ZR-75 was exposed to 5 μM MK 886 or NDGA for 24 and 48 hours, an up-regulation of both PPARα and PPARγ expression occurred. The biggest increase could be observed after 48-hour exposure with both inhibitors (FIG. 1 A–D).

Effect of PPAR ligands on breast tumor cell growth

To further evaluate the possible involvement of PPAR in growth regulation of cancer cells, a range of selective PPAR agonists was tested for their effect on breast cancer cell lines. This panel included ligands for PPARα (WY-14643, clofibrate, fenofibrate), as well as PPARγ (LY 171883). When breast cancer cell lines T47D and ZR-75 were incubated with each of the four PPAR ligands, a dose dependent growth reduction was observed with all the compounds for both cell lines compared to vehicle control (FIG. 1 E, F). At the higher doses, growth inhibition ranging from 60–80% were observed.

Interaction of PPAR effects on breast cancer cell growth:

Since the induction of PPARs occurs promptly with exposure to 5-LO inhibitors, breast cancer cell growth regulation was explored further to determine the involvement of PPAR induction. From the Northern blot analysis (FIG. 2A), induction of PPARγ is evident within six hours of exposure of T47D cells to the most potent 5-LO inhibitor, MK886. This finding is confirmed by semi-quantitative RT-PCR for PPARγ (FIG. 2B) but in these experiments the induction of PPARγ is more protracted. The up-regulation of PPARγ was less pronounced in the growth inhibition of the T47D cells. As shown in FIG. 2C, the filled circles represent cells exposed sequentially for twelve hours to 5 μM MK886 and then for twenty four hours to 4 μM LY 171883, PPARγ ligand. The sequential exposure to the FLAP inhibitor followed by the PPARγ ligand is associated with significantly more growth inhibition than exposure to the ligand alone or the FLAP inhibitor alone for the same amount of time. Under the same experimental conditions, the impact of the sequential exposure of these drugs on apoptosis as reported in FIG. 2D was evaluated. Similarly, the combined drug exposure was more potent that either single drug exposure. These experiments suggest that the consequences of endoperoxide shunting can generate products that could interact with the up-regulated PPARγ and have significant growth effects potentially through enhanced apoptosis.

EXAMPLE 3

Northern Blot Analysis

After treatment for the indicated time points (5 μM MK886 at 0, 6, 12, 24 hours), cells were washed with PBS and total RNA was extracted using the RNeasy Mini Kit (QUIAGEN Inc., Valencia, Calif.). Ten μg of RNA were loaded per lane, run in 1% agarose gels containing 2.2 M formaldehyde, blotted by capillarity onto nitrocellulose membranes (Schleicher & Schuell Inc., Keenee, N.H.), and baked for two hours at 80° C. Equal loading and integrity of RNA was monitored by ethidium bromide staining (FIG. 2A).

The human PPARγ cDNA probe (Cayman Chemicals, Ann Arbor, Mich.) was labeled with $[\gamma^{-32}P]dCTP$ (3000 Ci/mmol; NEN life Science Products, Boston, Mass.) by random priming. Unincorporated label was removed by Probe Quant G-50 Micro Columns (Amersham Pharmacia Biotech, Piscataway,N.J.). Hybridization was carried out overnight at 42° C. in Hybrisol 1(Intergen Inc., Purchase, N.Y.). After stringency washes, blots were exposed to XAR film. FIG. 2A shows the Northern blot results where PPARγ expression levels increase upon MK886 treatment.

EXAMPLE 4

PPAR Analysis in Lung Cancer

Lung cancer cell lines used for PPAR analysis included A549, H510, H345, and N417. The FLAP inhibitor: MK886 and COX inhibitor: indomethacin, and combinations thereof, were used as AA inhibitors. PPARs for the analysis included PGJ2 (γ ligand); ciglitazone (γ agonist); LY171882 (γ receptor activator); and WY 14643 (α activator). In order to analyze PPARs in lung cancer cells, growth inhibition (MTT, BrdU); apoptosis (Caspase 3/7 and M30 IHC); and mRNA Northern analyses were performed.

The results of the growth assays suggested that MK886 inhibited all tested cell lines in a dose dependent manner ranging from 0.25 to 2.0 μM; whereas, indomethacin had no effect on growth, even at a concentration of greater than 10 μM. The combination of MK886 and indomethacin on all cell lines tested resulted in growth inhibition greater than the growth inhibition seen with MK886 alone. PGJ2 and ciglitazone reduced growth in a dose dependent manner on the tested cell lines. LY171882 and WY 14643 had minimal effect on cell growth, i.e. less than 10%. The combination of MK886 and PGJ2 or MK886 and ciglitazone, as well as the combination of indomethacin and PGJ2 or indomethacin and ciglitazone resulted in reduced growth, which was more pronounced than either drug alone. In fact, an even greater reduction in growth was observed in most experiments when MK886, indomethacin, and PPAR ligand were combined.

Apoptosis was determined at particular time points using the Apo-1Caspase 3/7 assay. MK886 and the combination of MK886 and indomethacin generally resulted in increased apoptosis in the A549 cell line. When the N417 cell line was treated with MK886, a two fold increase in apoptosis was observed. A two fold induction of apoptosis was also observed after treatment with MK886, indomethacin, MK886 and PGJ2, or indomethacin and PGJ2 in the H510 cell line. MK886 induced apoptosis in the H345 cell line, but when combined with PGJ2, there was no significant increase in apoptosis, rather a decrease in apoptosis was observed. Ciglitazone, but neither LY171882 or WY 14643 (α activator) induced apoptosis in the H345 cell line, which has mRNA for PPARα.

M30 Immunohistochemistry was performed to test for apoptosis in the various lung cancer cell lines. Apoptosis was observed in the A549 cell line, where these results correlated to the growth inhibition results. Some apoptosis also occurred after treatment with LY171882. Apoptosis was also observed in the H345 and N417 cell lines, but PPAR induction was low and no significant increase in PPAR protein expression was observed when tested in combination with PGJ2. Furthermore, apoptosis in the H510 cell line was observed after administration of MK886, indomethacin, or PGJ2, and combinations thereof. In summary, combinations of FLAP inhibitors, cyclooxygenase inhibitors, and PPARγ ligands generally had additive effects in reducing lung cancer cell line growth; this generally correlated with measures of enhanced apoptosis.

Northern analysis was performed with untreated cells and cells treated with AA inhibitors: MK886, indomethacin, or the combination of MK886 and indomethacin. Up-regulation of PPARγ was observed in the A549 cell line after treatment with either of the AA inhibitors or combinations thereof. However, after the addition of PGJ2, the mRNA decreases to those levels observed with control. There was no mRNA for PPARα and some mRNA observed for PPARδ when induced with MK886. No PPARα or PPARγ expression was observed in untreated N417 cells. There was also no expression after 24 hours of exposure to AA inhibitors, confirming previous Northern analyses. Upon MK886 and PGJ2 treatment, PPARδ message was observed. In the H510 cell line, no expression for PPARγ was observed. However, low expression for PPARα was observed in untreated H510 cells, and up regulation of PPARα resulted after the addition of MK886 and PGJ2. Low PPARγ expression was observed in untreated H345 cells, and down regulated mRNA after administration with PGJ2. PPARγ expression was induced in H345 cells by MK886 treatment. Strong mRNA expression was observed for PPARα in untreated H345 cells, but down regulated after treatment with MK886 and PGJ2. No PPARδ was observed in H510 cells.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Menick, H., Jessup, J., Eyre, H., Cunningham, M., Fremgen, A., Murphy, G., and Winchester, D. (1997) Clinical highlights from the National Cancer Data Base. *CA Cancer J. Clin.* 47, 161–170.
2. Meade, E., McIntyre, T., Zimmerman, G., and Prescott, S. (1999) Peroxisome proliferators enhance cycooxygenase-2 expression in epithelial cells. *J Biol Chem* 274, 8328–8334.
3. Yano, T., Pinski, J., Groot, K., and Schally, A. (1992) Stimulation by bombesin and inhibition by bombesin/gastrin-releasing peptide antagonist RC-3095 of growth of human breast cancer cell lines. *Cancer Res* 52, 4545–4547.
4. Martin, J., J A Coverley, Pattison, S., and Baxter, R. (1995) Insulin-like growth factor-binding protein-3 production by MCF-7 breast cancer cells: Stimulation by retinoic acid and cyclic adenosine monophosphate and different effects of estradiol. *Endocrinology* 136, 1219–1226.
5. Thompson, C. (1995) Apoptosis in the pathogenesis and treatment of disease. *Science* 267, 1456–1462.
6. Piazza, G., Rahm, A., Krutzsch, M., Sperl, G., Paranka, N., Gross, P., Brendel, K., Burt, R., Alberts, D., Pamukcu, R., and Ahnen, D. (1995) Anti-neoplastic drugs Sulindac Sulfide and Sulfone inhibit cell growth by inducing apoptosis. *Cancer Res* 55, 3110–3116.
7. Wang, T., and Phang, J. (1995) Effects of estrogen on apoptotic pathways in human breast cancer cell line MCF-7. *Cancer Res* 55, 2487–2489.
8. Cullen, K., Yee, D., Sly, W., Perdue, J., Hampton, B., Lippman, M., and Rosen, N. (1990) Insulin-like growth factor receptor expression and function in human breast cancer. *Cancer Res* 50, 48–53.
9. Yee, D., Rosen, N., Favoni, R., and Cullen, K. (1991) The insulin-like growth factors, their receptors, and their binding proteins in human breast cancer. *Cancer Treat Res* 53, 93–106.
10. Baserga, R. (1994) Oncogenes and the strategy of growth factors. *Cell* 79, 927–930.
11. Yee, D., Paik, S., Lebovic, G., Marcus, R., Favoni, R., Cullen, K., Lippman, M., and Rosen, N. (1989) Analysis of insulin-like growth factor gene expression in malignancy: evidence for a paracrine role in human breast cancer. *Mol Endocrinol* 3, 509–517.
12. Gooch, J. L., Van Den Berg, C. L., and Yee, D. (1999) Insulin-like growth factor (IGF)-I rescues breast cancer cells from chemotherapy-induced cell death—proliferative and anti-apoptotic effects. *Breast Cancer Res Treat* 56, 1–10.
13. Lee, A. V., Gooch, J. L., Oesterreich, S., Guler, R. L., and Yee, D. (2000) Insulin-like growth factor I-induced degradation of insulin receptor substrate 1 is mediated by the 26S proteasome and blocked by phosphatidylinositol 3'-kinase inhibition. *Mol Cell Biol* 20, 1489–1496.
14. Quinn, K., Treston, A., Unsworth, E., Miller, M., Vos, M., Griley, C., Battey, J., Mulshine, J., and Cuttitta, F. (1996) Insulin-like growth factor expression in human cancer cell lines. *J Biol Chem* 271, 11477–11483.
15. Avis, I. M., Jett, M., Boyle, T., Vos, M. D., Moody, T., Treston, A. M., Martinez, A., and Mulshine, J. L. (1996) Growth control of lung cancer by interruption of 5-lipoxygenase- mediated growth factor signaling. *J Clin Invest* 97, 806–813.
16. Earashi, M., Noguchi, M., Kinoshita, K., and Tanaka, M. (1995) Effects of eicosanoid synthesis inhibitors on the in vitro growth and prostaglandin E and Leukotrine B secretion of a human breast cancer cell line. *Oncology* 52, 150–155.
17. Noguchi, M., Rose, D., Earashi, M., and Miyazaki, I. (1995) The role of fatty acids and eicosanoid synthesis inhibitors in breast carcinoma. *Oncology* 52, 265–271.
18. Przylipiak, A., Hafner, J., Przylipiak, J., Kohn, F. M., Runnebaum, B., and Rabe, T. (1998) Influence of 5-lipoxygenase on in vitro growth of human mammary carcinoma cell line MCF-7. *Gynecol Obstet Invest* 46, 61–64.

19. Dixon, R., Jones, R., Diehl, R., Bennett, C., Kargman, S., and Rouzer, C. (1988) Cloning of cDNA for human 5-lipoxygenase. *Proc Natl Acad Sci USA* 85, 416–420.

20. Ford-Hutchinson, A. (1994) Regulation of leukotriene biosynthesis. *Cancer and Metastasis Reviews* 13, 257–267.

21. Dubois, R., Abramson, S., Crofford, L., Gupta, R., Simon, L., Putte, L. V. D., and Lipsky, P. (1998) Cyclooxygenase in biology and disease. *FASEB J* 12, 1063–1073.

22. Hong, S. H., Avis, I., Vos, M. D., Martinez, A., Treston, A. M., and Mulshine, J. L. (1999) Relationship of arachidonic acid metabolizing enzyme expression in epithelial cancer cell lines to the growth effect of selective biochemical inhibitors. *Cancer Res* 59, 2223–2228.

23. Peters-Golden, M. and Brock T. G., (2000) Intracellular compartmentalization of leukotriene biosynthesis. *Am J Respir Crit Care Med* 16]:S36-40.

24. Boyle, T., Lancaster, V., Hunt, R., Gemski, P., and Jett, M. (1994) Method for simultaneous quantitation of platelet activating factor and multiple arachidonate metabolites from small samples: analysis of effects of staphylococcus aureus enterotoxin B in mice. *Anal. Biochem.* 216, 373–382.

25. Monaghan, P., Robertson, D., Amos, T., Dyer, M., Mason, D., and Greaves, M. (1992) Ultrastructural localization of bcl-2 protein. *J Histochem Cytochem* 40, 1819–1825.

26. Datta, K., Biswal, S. S., and Kehrer, J. P. (1999) The 5-lipoxygenase-activating protein (FLAP) inhibitor, MK886, induces apoptosisindependently of FLAP. *Biochem. J.* 340:371–375.

27. Mueller et al., (1998) Terminal differentiation of human breast cancer through PPAR gamma. *Mol. Cell.,* 1:465–470.

28. Kitamura et al., (1999) Increased expression of cyclooxygenases and peroxisome proliferator-activated receptor-gamma in Alzheimer's disease brains. *Biochem. Biophys. Res. Commun.,* 254:582–586.

29. Sarraf et al., (1999) Loss-of-function mutations in PPAR gamma associated with human colon cancer. *Mol. Cell.,* 3:799–804.

30. Gillard et al. (1989) L-663,536 (MK-886) (3-[1-(4-chlorobenzyl)-3-t-butyl-thio-5-isopropylindol-2-yl]-2,2-dimethylpropanoic acid), a novel, orally active leukotriene biosynthesis inhibitor. *Can J. Physiol. Pharmacol* 67:456–464.

31. Rouzer, et al. (1990) MK886, a potent and specific leukotriene biosynthesis inhibitor blocks and reverses the membrane association of 5-lipoxygenase in ionophore-challenged leukocytes. *J. Biol. Chem.* 265:1436–1442.

32. Tagari, et al. (1993) Assessment of the in vivo biochemical efficacy of orally active leukotriene biosynthesis inhibitors. *Agents Actions* 40:62–71.

33. Wang, et al. (1991) Antimutagenic and antitumorigenic activities of nordihydroguaiaretic acid. *Mutation Research* 261:153–162.

34. Salari, et al. (1984) Comparative effects of indomethacin, acetylenic acids, 15-HETE, nordihydroguaiaretic acid and BW755C on the metabolism of arachidonic acid in human leukocytes and platelets. *Prostoglandins Leukotrienes And Medicine* 13:53–60.

35. Yoshimoto, et al. (1982) 2,3,5-Trimethyl-6-(12-hydroxy-5,10-dodecadiynyl)-1,4-benzoquinone (AA861), a selective inhibitor of the 5-lipoxygenase reaction and the biosynthesis of slow-reacting substance of anaphylaxis. *Biochemical Biophysica ACTA* 713:470–473.

36. Ashida, Y, et al. (1983) Pharmacological profile of AA-861, a 5-lipoxygenase inhibitor. *Prostoglandins* 26(6):955–972.

37. Kubota et al. Ligand for peroxisome proliferator-activated receptor gamma (troglitazone) has potent antitumor effect against human prostate cancer both in vitro and in vivo. *Cancer Res.,* 1998, 58:3344–3352.

38. Lehmann et al. (1995) An antidiabetic thiazolidinedione is a high affinity ligand for peroxisome proliferator-activated receptor gamma (PPAR gamma). *J. Biol. Chem.,* 270:12953–12956.

39. Mizukami and Taniguchi. (1997) The antidiabetic agent thiazolidinedione stimulates the interaction between PPAR gamma and CBP. *Biochem. Biophys. Res. Commun.,* 240:61–64.

40. Murakami et al. (1998) A novel insulin sensitizer acts as a coligand for peroxisome proliferator-activated receptor-alpha (PPAR-alpha) and PPAR-gamma: effect of PPAR-alpha activation on abnormal lipid metabolism in liver of Zucker fatty rats. *Diabetes,* 47:1841–1847.

41. Reginato et al. (1998) A potent antidiabetic thiazolidinedione with unique peroxisome proliferator-activated receptor gamma-activating properties. *J. Biol. Chem.,* 273:32679–32684.

42. Spiegelman (1998) PPAR-gamma: adipogenic regulator and thiazolidinedione receptor. *Diabetes,* 47:507–514.

43. Berger et al. (1999) Novel peroxisome proliferator-activated receptor (PPAR) gamma and PPARdelta ligands produce distinct biological effects. *J. Biol. Chem.,* 1999, 274:6718–6725.

44. Elbrecht et al. (1999) L-764406 is a partial agonist of human peroxisome proliferator-activated receptor gamma. The role of Cys313 in ligand binding. *J. Biol. Chem.,* 274:7913–7922.

45. Palmer and Wolf (1998) cis-parinaric acid is a ligand for the human peroxisome proliferator activated receptor gamma: development of a novel spectrophotometric assay for the discovery of PPARgamma ligands. *FEBS Lett.,* 431:476–480.

46. Forman et al. (1995) 15-Deoxy-delta 12, 14-prostaglandin J2 is a ligand for the adipocyte determination factor PPAR gamma. *Cell,* 83:803–812.

47. Kliewer et al. (1995) A prostaglandin J2 metabolite binds peroxisome proliferator-activated receptor gamma and promotes adipocyte differentiation. *Cell,* 83:813–819.

48. Huang, J. T., Welch, J. S., Ricote, M., Binder, C. J., Willson, T. M., Kelly, C., Witztum, J. L., Funk, C. D., Conrad, D., and Glass, C. K. (1999) Interleukin-4-dependent production of PPAR-gamma ligands in macrophages by 12/15-lipoxygenase. *Nature* 400:378–382.

What is claimed is:

1. A method of treating an epithelial cell-derived cancer in a subject comprising administering to the subject an inhibitor to an enzyme that metabolizes arachidonic acid and a PPAR ligand, or derivative thereof, in an amount effective for the treatment of the epithelial cell-derived cancer in the subject.

2. The method of claim 1, wherein the inhibitor is a 5-lipoxygenase inhibitor.

3. The method of claim 2, wherein the inhibitor is 3-2,2-dimethylpropanoic acid or derivative thereof.

4. The method of claim 1, wherein the PPAR ligand is a PPARγ ligand.

5. The method of claim 4, wherein the PPARγ ligand is LY171883 or derivative thereof.

6. The method of claim 1, wherein the inhibitor and PPAR ligand or derivative thereof are added sequentially.

7. The method of claim 1, wherein the epithelial cell-derived cancer is breast cancer or lung cancer.

8. The method of claim 1, wherein the epithelial cell-derived cancer is selected from the group consisting of prostate cancer, colon cancer, uterine cancer, and cervical cancer.

9. The method of claim 1, wherein the administration is by aerosol delivery.

10. A method of preventing an epithelial cell-derived cancer in a subject comprising administering to the subject an inhibitor to an enzyme that metabolizes arachidonic acid and a PPAR ligand, or derivative thereof, in an amount effective for the prevention of the epithelial cell-derived cancer in the subject.

11. The method of claim 10, wherein the inhibitor is a 5-lipoxygenase inhibitor.

12. The method of claim 11, wherein the inhibitor is 3-2,2-dimethylpropanoic acid or derivative thereof.

13. The method of claim 10, wherein the PPARγ ligand is a PPARγ ligand.

14. The method of claim 13, wherein the PPARγ ligand is LY 171883 or derivative thereof.

15. The method of claim 10, wherein the inhibitor and PPAR ligand or derivative thereof are added sequentially.

16. The method of claim 10, wherein the epithelial cell-derived cancer is breast cancer or lung cancer.

17. The method of claim 10, wherein the epithelial cell-derived cancer is selected from the group consisting of prostate cancer, colon cancer, uterine cancer, and cervical cancer.

18. The method of claim 10, wherein the administration is by aerosol delivery.

19. A method of preventing or treating the growth of epithelial cell-derived cancer cells in a subject in need thereof by administering an inhibitor to an enzyme that metabolizes arachidonic acid and a PPAR ligand in an amount effective to induce apoptosis.

20. The method of claim 19, wherein the inhibitor is a 5-lipoxygenase inhibitor.

21. The method of claim 20, wherein the inhibitor is 3-2,2-dimethylpropanoic acid or derivative thereof.

22. The method of claim 19, wherein the PPAR ligand is a PPARγ ligand.

23. The method of claim 22, wherein the PPARγ ligand is LY171883 or derivative thereof.

24. The method of claim 19, wherein the inhibitor and PPAR ligand are added sequentially.

25. The method of claim 19, wherein the epithelial cell-derived cancer is breast cancer or lung cancer.

26. The method of claim 19, wherein the epithelial cell-derived cancer is selected from the group consisting of prostate cancer, colon cancer, uterine cancer, and cervical cancer.

27. The method of claim 19, wherein the administration is by aerosol delivery.

28. A pharmaceutical composition comprising an inhibitor to an enzyme that metabolizes arachidonic acid and a PPAR ligand, or derivatives thereof, and a pharmaceutically-acceptable carrier.

29. The pharmaceutical composition according to claim 28, wherein the inhibitor is a 5-lipoxygenase inhibitor, or derivative thereof.

30. The pharmaceutical composition according to claim 29, wherein the inhibitor is 3-2,2-dimethylpropanoic acid or derivative thereof.

31. The pharmaceutical composition according to claim 29, wherein the PPAR ligand is a PPARγ ligand.

32. The pharmaceutical composition according to claim 31, wherein the PPAR ligand is LY171883 or derivative thereof.

33. The pharmaceutical composition according to claim 28, wherein the carrier is an excipient.

34. The pharmaceutical composition according to claim 28, wherein the carrier is a diluent.

35. The method of claim 1, wherein the inhibitor is a 5-lipoxygenase inhibitor or a cyclooxygenase inhibitor.

36. The method of claim 35, wherein the inhibitor is MK886, MK-591, NDGA, AA861, L-669,572, L-663,511, L-665,210, L-654-639, L-668,017, Zileuton, or indomethacin.

37. The method of claim 2, wherein the inhibitor is MK886, MK-591, NDGA, AA861, L-669,572, L-663,51 1, L-665,210, L-654-639, L-668,017, or Zileuton.

38. The method of claim 37, wherein the PPAR ligand is WY-14643, clofibrate, fenofibrate, LY 171883, 1 5d-PGJ$_2$, ciglitazone, or troglitazone.

39. The method of claim 6, wherein the inhibitor is administered to the subject prior to administration of the PPAR ligand.

40. The method of claim 39, wherein the inhibitor is administered continuously for 6–48 hours and the PPALR ligand is administered continuously for 24 hours.

41. The method of claim 39, wherein the inhibitor is a 5-lipoxygenase inhibitor or a cyclooxygenase inhibitor.

42. The method of claim 41, wherein the PPAR ligand is a PPARy ligand.

43. The method of claim 42, wherein the inhibitor is MK886.

44. The method of claim 43, wherein the PPAR ligand is LY 171883.

45. The method of claim 44, wherein the cancer is breast cancer.

46. The method of claim 42, wherein the inhibitor is indomethacin.

47. The method of claim 46, wherein the PPAR ligand is 15d-PGJ$_2$ or cightazone.

48. The method of claim 47, wherein the cancer is lung cancer.

49. A method of treating an epithelial cell derived cancer in a subject comprising, administering to the subject a combination of a lipoxygenase and a cyclooxygenase inhibitor in an amount effective for the treatment of epithelial cell derived cancer in the subject.

50. The method of claim 49, wherein the lipoxygenase inhibitor is a 5 -lipoxygenase inhibitor.

51. The method of claim 50, wherein the 5-lipoxygenase inhibitor is MK886, MK-591, NDGA, AA861, L-669,572, L-663,511, L-665,210, L-654-639, L-668,017, or Zileuton.

52. The method of claim 51, wherein the cyclooxygenase inhibitor is indomethacin.

53. The method of claim 49, further comprising administering a PPAR ligand to the subject in an amount effective for the treatment of epithelial cell derived cancer in the subject.

54. The method of claim 53, wherein the PPAR ligand is WY-14643, clofibrate, fenofibrate, LY 171883, 15d-PGJ$_2$, ciglitazone, or troglitazone.

55. The method of claim 54, wherein the combination of the lipoxygenase inhibitor and the cyclooxygenase inhibitor is administered prior to administration of the PPAR ligand.

* * * * *

UNITED STATES PATENT AND TRADEMARK OFFICE
CERTIFICATE OF CORRECTION

PATENT NO.    : 6,756,399 B2
DATED         : June 29, 2004
INVENTOR(S)   : Mulshine et al.

It is certified that error appears in the above-identified patent and that said Letters Patent is hereby corrected as shown below:

Column 6,
Line 40, "PPAR γ" should read -- PPARγ --.

Column 7,
Line 48, "coca" should read -- cocoa --.

Column 9,
Line 63, "that" should read -- than --.

Column 11,
Line 66, (Ref. 2), "cycooxygenase" should read -- cyclooxygenase --

Column 13,
Line 22, (Ref. 23), "16]" should read -- 161 --.
Line 35, (Ref. 26), "apoptosisindependently" should read -- apoptosis independently --.

Column 14,
Line 39, (Ref. 43), "PPARdelta" should read -- PPAR-delta--.
Line 49, (Ref. 45), "PPARgamma" should read -- PPAR-gamma --.

Column 15,
Line 56, "3-2,2-dimethylpropanoic" should read -- 3-[1-(4-chlorobenzyl)-3-t-butyl-thio-5-isopropylindol-2-yl]-2, 2-dimethylpropanoic --.

Column 16,
Line 49, "preventing" should read -- inhibiting --.
Line 53, "prevention" should read -- inhibition --.
Line 58, "3-2,2-dimethylpropanoic" should read -- 3-[1-(4-chlorobenzyl)-3-t-butyl-thio-5-isopropyl-indol-2-yl]-2,2-dimethylpropanoic --.
Line 59, "PPARγ" should read -- PPAR --.

Column 17,
Line 7, "preventing" should read -- inhibiting --.
Lines 15 and 38, "3-2,2-dimethylpropanoic" should read -- 3-[1-(4-chlorobenzyl)-3-t-butyl-thio-5-isopropyl-indol-2-yl]-2,2-dimethylpropanoic --.

UNITED STATES PATENT AND TRADEMARK OFFICE
CERTIFICATE OF CORRECTION

PATENT NO. : 6,756,399 B2
DATED : June 29, 2004
INVENTOR(S) : Mulshine et al.

It is certified that error appears in the above-identified patent and that said Letters Patent is hereby corrected as shown below:

Column 18,
Line 11, "PPALR" should read -- PPAR --.
Line 11, "PPARY" should read -- PPARγ --.
Line 26, "cightazone" should read -- ciglitazone --.

Signed and Sealed this

Twenty-sixth Day of July, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 1
ggcctcaggc tatcattac                                               19

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 2
ccatttccat acgctacc                                                18

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 3
ttcaaacaca tcaccccccc                                              19

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 4
ttgccaagtc gctgtcatc                                               19